US010755408B2

(12) United States Patent
Sakurai et al.

(10) Patent No.: US 10,755,408 B2
(45) Date of Patent: Aug. 25, 2020

(54) MEDICAL INFORMATION PROCESSING SYSTEM AND MEDICAL INFORMATION PROCESSING APPARATUS

(71) Applicant: Canon Medical Systems Corporation, Otawara-shi (JP)

(72) Inventors: Yasuo Sakurai, Nasushiobara (JP); Masahiro Ozaki, Otawara (JP); Atsuko Sugiyama, Nasushiobara (JP); Seiko Yoshimura, Nasushiobara (JP); Keisuke Hashimoto, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 100 days.

(21) Appl. No.: 15/972,598

(22) Filed: May 7, 2018

(65) Prior Publication Data
US 2018/0330500 A1    Nov. 15, 2018

(30) Foreign Application Priority Data

May 9, 2017   (JP) .................. 2017-092972
Apr. 27, 2018   (JP) .................. 2018-086986

(51) Int. Cl.
G06T 7/00    (2017.01)
A61B 5/00    (2006.01)
(Continued)

(52) U.S. Cl.
CPC .......... G06T 7/0012 (2013.01); A61B 5/0033 (2013.01); G06T 7/0016 (2013.01);
(Continued)

(58) Field of Classification Search
CPC ................ G06T 7/0012; G06T 7/35; G06T 2207/10081; G06T 2207/10088;
(Continued)

(56) References Cited

U.S. PATENT DOCUMENTS 6,055,449 A * 4/2000 Navab .............. A61B 6/12
378/98.12
6,282,305 B1 * 8/2001 Huo ................ G06T 7/0012
382/128
(Continued)

FOREIGN PATENT DOCUMENTS

JP    2002-517836    6/2002
JP    5094770    12/2012
(Continued)

Primary Examiner — Khai M Nguyen
(74) Attorney, Agent, or Firm — Oblon, McClelland, Maier & Neustadt, L.L.P.

(57) ABSTRACT

A medical information processing system according to an embodiment includes processing circuitry. The processing circuitry is configured to identify the position of a tissue from first medical image data represented by an image of a target site acquired before the tissue in the target site was collected and to obtain an image feature value of the tissue. The processing circuitry is configured to obtain an examination result of a pathological examination performed on the tissue. The processing circuitry is configured to bring the image feature value of the tissue into association with the examination result of the pathological examination.

13 Claims, 9 Drawing Sheets

(51) Int. Cl.
*G16H 40/63* (2018.01)
*G16H 30/40* (2018.01)
*G06T 7/35* (2017.01)
*G16H 50/20* (2018.01)
*G06K 9/62* (2006.01)

(52) U.S. Cl.
CPC .............. *G06T 7/35* (2017.01); *G16H 30/40* (2018.01); *G16H 40/63* (2018.01); *G16H 50/20* (2018.01); *G06K 9/6277* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/20104* (2013.01); *G06T 2207/20224* (2013.01); *G06T 2207/30004* (2013.01); *G06T 2207/30024* (2013.01); *G06T 2207/30096* (2013.01); *G06T 2207/30204* (2013.01)

(58) Field of Classification Search
CPC . G06T 2207/10104; G06T 2207/10108; G06T 2207/10116; G06T 2207/20104; G06T 2207/20224; G06T 2207/30004; G06T 2207/30024; G06T 2207/30096; G06T 2207/30204; G16H 50/20; G16H 30/40; G16H 40/63; A61B 5/0033; G06K 9/6277
See application file for complete search history.

(56) References Cited

U.S. PATENT DOCUMENTS

| | | | |
|---|---|---|---|
| 2010/0088264 A1* | 4/2010 | Teverovskiy | G16H 50/20 706/46 |
| 2010/0303330 A1* | 12/2010 | Moriya | G16H 40/63 382/132 |

FOREIGN PATENT DOCUMENTS

| | | |
|---|---|---|
| JP | 5094775 | 12/2012 |
| WO | WO 99/63480 A1 | 12/1999 |

* cited by examiner

FIG.4

| CLINICAL CASES | SCORE (MARKER A) | FEATURE VALUE A | FEATURE VALUE B | FEATURE VALUE C | FEATURE VALUE D | FEATURE VALUE E | FEATURE VALUE F | ... |
|---|---|---|---|---|---|---|---|---|
| 1 | 4 | 1 | 1 | 5 | 2 | 0 | 1 | ... |
| 2 | 5 | 4 | 1 | 4 | 3 | 1 | 2 | ... |
| 3 | 1 | 0 | 0 | 2 | 5 | 5 | 3 | ... |
| ⋮ | ⋮ | ⋮ | ⋮ | ⋮ | ⋮ | ⋮ | ⋮ | ⋮ |

MEDICAL INFORMATION PROCESSING SYSTEM AND MEDICAL INFORMATION PROCESSING APPARATUS

CROSS-REFERENCE TO RELATED APPLICATIONS

This application is based upon and claims the benefit of priority from Japanese Patent Application No. 2017-92972, filed on May 9, 2017; and Japanese Patent Application No. 2018-86986, filed on Apr. 27, 2018, the entire contents of all of which are incorporated herein by reference.

FIELD

Embodiments described herein relate generally to a medical information processing system and a medical information processing apparatus.

BACKGROUND

In recent years, mechanisms of diseases and medicinal effects have been analyzed on the basis of molecular biology, so that accumulated findings started being applied to clinical examinations. In particular, in the field of pathology, many medical examinations are being performed to detect expression of a certain protein or gene (which hereinafter may be referred to as a molecule marker) that is specific to a certain disease or pathological condition and from which it is expected to be possible to predict a prognosis or medicinal effects. These examinations are performed while using a part of a tissue of a lesion collected in surgery or a biopsy as a specimen. However, such a molecular marker is not necessarily always expressed in the tissue of the lesion in a homogeneous manner. For this reason, there is a possibility that the examination result may exhibit a false-positive or a false-negative.

To solve this problem, attempts have been made to link examination results based on medical images rendering the entirety of a tissue of a lesion and being acquired by a Computed Tomography (CT) apparatus, a Magnetic Resonance Imaging (MRI) apparatus, a nuclear medical apparatus, or the like to examination results based on pathological molecular markers, so as to utilize the linked information for diagnosis purposes. This field may be called radiomics, for example.

BRIEF DESCRIPTION OF THE DRAWINGS

FIG. 4 is a table illustrating an example of relevance information according to the first embodiment;

DETAILED DESCRIPTION

A medical information processing system according to an embodiment includes processing circuitry. The processing circuitry is configured to identify the position of a tissue from first medical image data represented by an image of a target site acquired before the tissue in the target site was collected and to obtain an image feature value of the tissue. The processing circuitry is configured to obtain an examination result of a pathological examination performed on the tissue. The processing circuitry is configured to bring the image feature value of the tissue into association with the examination result of the pathological examination.

Exemplary embodiments of a medical information processing system and a medical information processing apparatus of the present disclosure will be explained in detail below, with reference to the accompanying drawings. In the following sections, although a medical information processing system including a medical information processing apparatus that has functions of the medical information processing apparatus according to the present disclosure will be explained as the exemplary embodiments, possible embodiments of the medical information processing system and the medical information processing apparatus of the present disclosure are not limited to those described below.

First Embodiment

Figure 1:
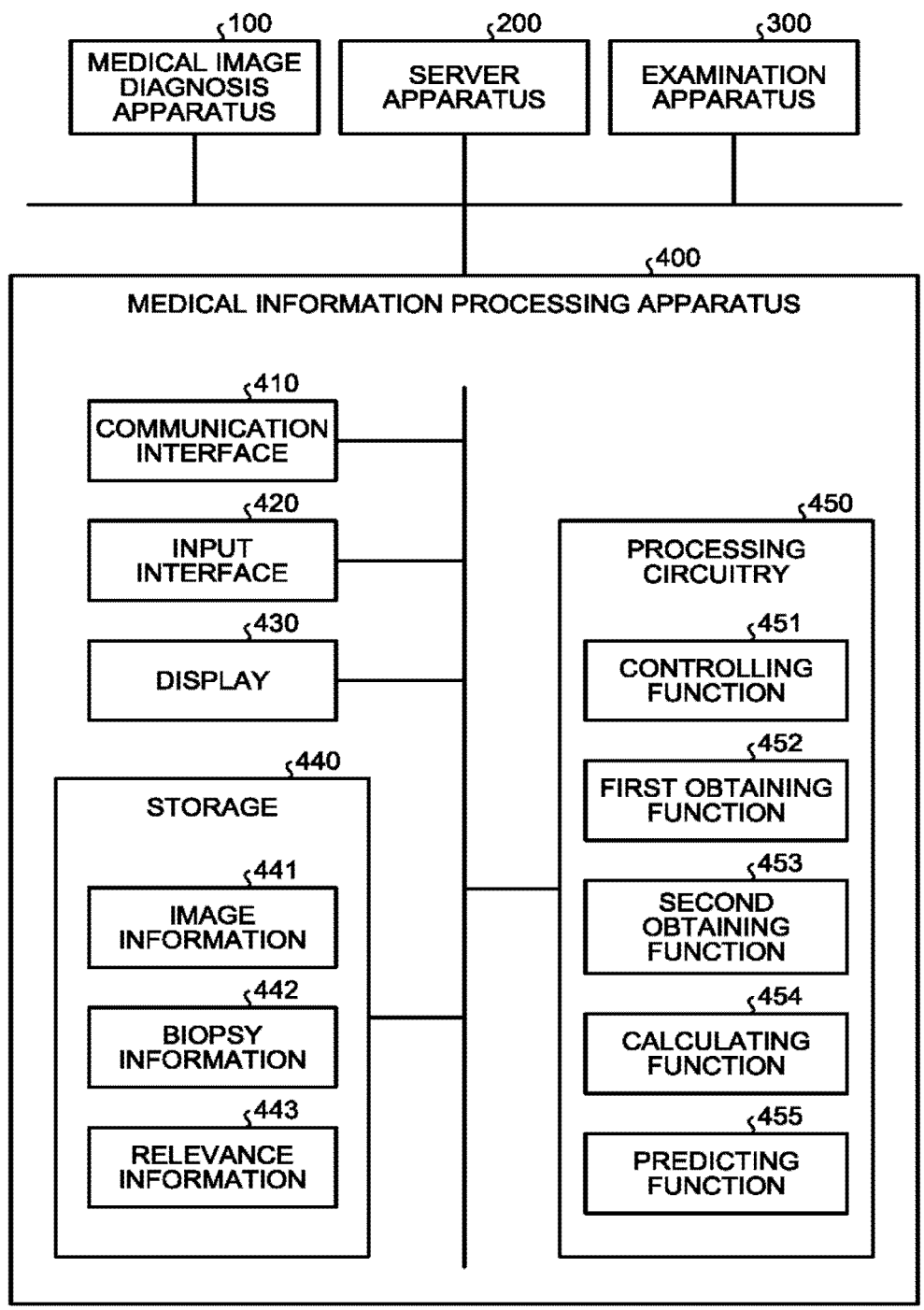
FIG. 1 is a diagram illustrating an exemplary configuration of a medical information processing system including a medical information processing apparatus according to a first embodiment.

First, a configuration of a medical information processing system including a medical information processing apparatus according to the first embodiment will be explained. FIG. 1 is a diagram illustrating an exemplary configuration of the medical information processing system including the medical information processing apparatus according to the first embodiment. For example, as illustrated in FIG. 1, the medical information processing system according to the first embodiment includes a medical image diagnosis apparatus 100, a server apparatus 200, a medical examination apparatus (hereinafter, "examination apparatus") 300, and a medical information processing apparatus 400. The apparatuses are connected to one another via a network. The medical information processing system may further have connected thereto one or more other information processing apparatuses such as a user terminal, for example, via a network.

The medical image diagnosis apparatus 100 may be any of the following: an X-ray diagnosis apparatus, an X-ray Computed Tomography (CT) apparatus, a Magnetic Resonance Imaging (MRI) apparatus, an ultrasound diagnosis apparatus, a Single Photon Emission Computed Tomography (SPECT) apparatus, a Positron Emission Tomography (PET) apparatus, a SPECT-CT apparatus in which a SPECT apparatus and an X-ray CT apparatus are integrated together, a PET-CT apparatus in which a PET apparatus and an X-ray CT apparatus are integrated together, and a group made up of any of these apparatuses. The medical image diagnosis apparatus 100 is configured to acquire medical image data of an examined subject (a target site of an examined subject) and to generate a display-purpose medical image from the acquired medical image data. Further, the medical image diagnosis apparatus 100 arranges the generated medical image to be displayed on a display device thereof or the like. Further, the medical image diagnosis apparatus 100 transmits the acquired medical image data and/or the generated medical image to any of the apparatuses connected to the network.

For example, the medical image diagnosis apparatus 100 is configured to acquire medical image data taken before and after a biopsy of mutually the same examined subject (hereinafter, "patient"). In other words, with respect to the same patient, the medical image diagnosis apparatus 100 acquires medical image data of the target site before a tissue is collected therefrom and medical image data of the target site after the tissue is collected therefrom. In this situation, as the medical image diagnosis apparatus 100, mutually-different apparatuses may acquire the pieces of medical image data from the same target site of the same patient. For example, an X-ray CT apparatus, an MRI apparatus, and a PET apparatus acquire the pieces of medical image data before and after the biopsy from the same target site of the same patient. In the following sections, various types of images acquired by mutually-different apparatuses each serving as the medical image diagnosis apparatus 100 (e.g., CT images acquired by the X-ray CT apparatus and MR images acquired by the MRI apparatus) and various types of images acquired by mutually the same apparatus may be referred to as "image types".

In this situation, the medical image diagnosis apparatus 100 is capable of obtaining various types of information depending on the imaging taking method being used. For example, the MRI apparatus is capable of measuring a relaxation time period of hydrogen atoms in the body of a patient through various image taking sequences and is capable of estimating, on the basis of the length of the relaxation time period, the presence of a biopolymer such as a protein and the presence of a pathological condition such as an inflammation or an edema. Further, the MRI apparatus is also capable of obtaining information about the abundance ratio of a specific metabolite or a pH value in an image taking region. The X-ray CT apparatus is capable of obtaining electron density information of a tissue, by using a plurality of X-ray energy values. Further, the PET apparatus is capable of obtaining metabolic information of a plurality of polymers, by changing a tracer administered to the patient. The image types in the present embodiment also include various type of images used for obtaining any of the various types of information described above.

The server apparatus 200 is configured to store therein the medical image data acquired by any of the various types of medical image diagnosis apparatuses and to store therein relevance information generated by the medical information processing apparatus 400. For example, the server apparatus 200 is configured to obtain the medical image data and the medical images from the medical image diagnosis apparatus 100 via the network and to store the obtained medical image data and medical images into storage provided on the inside or the outside of the apparatus. Further, the server apparatus 200 is configured to obtain the relevance information from the medical information processing apparatus 400 via the network and to store the obtained relevance information into storage provided on the inside or the outside of the apparatus. Details of the relevance information will be explained later.

The examination apparatus 300 is configured to obtain medical examination information (hereinafter "examination information") (biopsy information) of a pathological examination and to store therein the obtained biopsy information or to transmit the biopsy information to the medical information processing apparatus 400. More specifically, the examination apparatus is configured to store therein the biopsy information performed on the tissue collected from the target site of the patient and to transmit the biopsy information to the medical information processing apparatus 400. For example, the examination apparatus 300 stores therein the biopsy information performed on the tissue collected from the target site from which the pieces of medical image data before and after the biopsy was acquired by the medical image diagnosis apparatus 100 and transmits the biopsy information to the medical information processing apparatus 400.

In this situation, examples of the pathological examination performed on the tissue collected from the target site include: a cytodiagnosis examination, a tissue examination, and a molecular pathological examination. For example, when a cytodiagnosis examination or a tissue examination is performed, a pathologist examines a specimen of the collected tissue or cells. In one example, the pathologist observes the specimen with a microscope and makes a morphological diagnosis as to judging whether a tumor is benign or malignant, the name of a diagnosed condition, the actual condition of a lesion, spreading of the lesion, and judging effectiveness of treatments and prognosis. The examination apparatus 300 receives these morphological diagnosis results and identification information (e.g., the patient's ID, an examination ID of the pathological examination, etc.) of the tissue (the cells) on which the pathological examination was performed, and further stores therein these pieces of information so as to be kept in correspondence with each other. Further, the examination apparatus 300 transmits the received diagnosis results, together with the identification information, to the medical information processing apparatus 400.

Further, for example, when a molecular pathological examination is performed, expression of a molecular marker (a certain protein or gene) is examined by implementing a method based on immunostaining, in-situ hybridization, a Reverse Transcription Polymerase Chain Reaction (RT-PCR), or the like while using the collected tissue or cells. In this situation, the molecular marker is a certain protein or gene that is specific to a certain disease or pathological condition and from which it is expected to be possible to predict a prognosis or medicinal effects. For example, in an immunostaining process, the expression of a molecular marker is examined by using an antigen-antibody interaction while using an antibody specific to a molecular marker (an antigen protein) at the tissue. In this situation, in the immunostaining process, the antigen-antibody interaction is made visible as being colored by a fluorescent antibody method, an enzyme antibody method, or the like. For example, the pathologist determines an expression intensity of the molecular marker on the basis of the number of cells exhibiting the color (being stained) and the level of the exhibition of the color (the staining).

Further, for example, during an in-situ hybridization process, the expression of a molecular marker is examined on the basis of the formation of a complex by the molecular marker and nucleic acid molecules, while using the nucleic acid molecules that are complementary to the molecular marker (a certain DNA or mRNA) in the tissue (the cells). In this situation, in an in-situ hybridization process, the formation of a complex by the molecular marker and the nucleic acid molecules may be detected by using a fluorescent substance or may be detected on the basis of immune-histochemistry. For example, the pathologist determines whether the expression of the molecular marker is positive/negative on the basis of whether the formation of a complex has occurred or not.

Further, for example, when a method based on an RT-PCR is used, RNA is extracted from the tissue, so as to synthesize cDNA from the RNA by using a reverse transcriptase. Further, while using the cDNA as a template, the expression of a molecular marker (a certain gene) is examined by implementing a real-time PCR while using a primer that has a sequence complementary to that of the molecular marker. In this situation, according to the method based on an RT-PCR, the amount of cDNA in the sample is reflected by the rising of an amplification curve in a real-time PCR. Because the amount of cDNA in the sample is proportional to the expression amount of the molecular marker, the speed of the rising of the amplification curve in the real-time PCR indicates the expression amount of the molecular marker. For example, the pathologist determines an expression intensity of the molecular marker on the basis of the expression amount of the molecular marker with respect to the expression amount of a gene serving as a control (a gene that is expressed by a certain amount regardless of diseases).

The examination apparatus 300 is configured to receive the examination result of the molecular pathological examination described above and the identification information of the tissue (the cells) on which the examination was performed and to store these pieces of information therein so as to be kept in correspondence with each other. Further, the examination apparatus 300 is configured to transmit the received examination result, together with the identification information, to the medical information processing apparatus 400. In this situation, the examination apparatus 300 is able to express the examination result of the molecular pathological examination by using a score. For example, when the immunostaining method is used, the examination apparatus 300 counts the number of cells corresponding to staining intensities on the six levels from 0 to 5 while giving a score of "5 points" to each of the cells stained with the highest intensity and calculates the "sum of (each staining intensity level×the number of cells)" as an expression intensity score of the molecular marker in the collected tissue.

Figure 2:
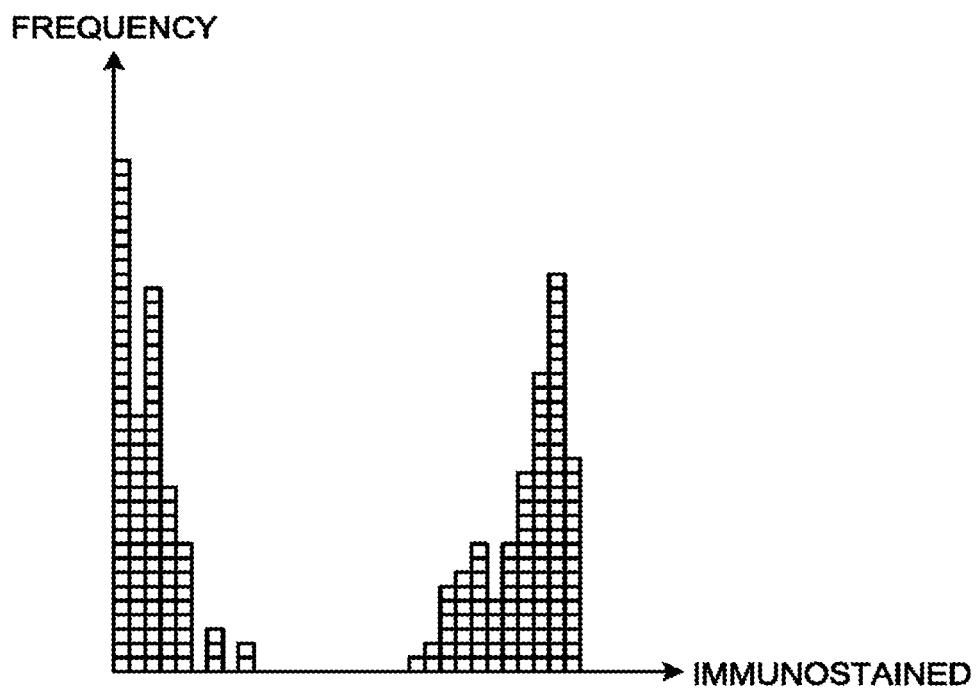
FIG. 2 is a chart for explaining a calculating process of an expression intensity score of a molecular marker realized by using immunostaining according to the first embodiment.

Next, the process of calculating the expression intensity score of the molecular marker by implementing immunostaining process will be explained with reference to FIG. 2. FIG. 2 is a chart for explaining the calculating process of the expression intensity score of the molecular marker realized by implementing the immunostaining process according to the first embodiment. FIG. 2 illustrates a histogram in which the horizontal axis expresses the staining intensities from the immunostaining process, whereas the vertical axis expresses the frequency. Further, FIG. 2 illustrates an example in which the staining intensities are not expressed on the six levels as explained above but are expressed in even finer levels. For example, the pathologist counts the number of cells on each of the staining intensity levels, while observing the immunostained tissue with a microscope. The examination apparatus 300 receives the counts from the pathologist and generates the histogram indicating the number of cells corresponding to each of the staining intensity levels, as illustrated in FIG. 2. Subsequently, when the pathologist has finished the courting process, the examination apparatus 300 calculates the expression intensity score of the molecular marker on the basis of the histogram. Further, the examination apparatus 300 transmits the calculated expression intensity score of the molecular marker to the medical information processing apparatus 400.

When an expression intensity score of a molecular marker is calculated while implementing an in-situ hybridization process, the examination apparatus 300 performs a calculation, for example, while giving a "score: 0" to the expression of the molecular marker being negative and giving a "score: 1" to the expression of the molecular marker being positive. As another example, when an expression intensity score of a molecular marker is calculated while implementing a method based on an RT-PCR, the examination apparatus 300 calculates, for example, a score corresponding to the ratio of the expression amount of the molecular marker to the expression amount of a gene serving as a control. Alternatively, for example, the examination apparatus 300 may perform a calculation, for example, while giving a "score: 0" to the expression of the molecular marker being negative and giving "score: 1" to the expression of the molecular marker being positive. After that, the examination apparatus 300 transmits the calculated expression intensity score of the molecular marker to the medical information processing apparatus 400.

Returning to the description FIG. 1, the medical information processing apparatus 400 includes a communication interface 410, an input interface 420, a display 430, storage 440, and processing circuitry 450. For example, the medical information processing apparatus 400 is realized by using a computer device such as a workstation.

The communication interface 410 is connected to the processing circuitry 450 and is configured to control the transfer of various types of data and communication performed among the medical image diagnosis apparatus 100, the server apparatus 200, and the examination apparatus 300 that are connected via the network. For example, the communication interface 410 is realized by using a network card, a network adaptor, a Network Interface Controller (NIC), or the like.

The input interface 420 is connected to the processing circuitry 450 and is configured to convert an input operation received from an operator into an electrical signal and to output the electrical signal to the processing circuitry 450. For example, the input interface 420 is realized by using a switch button, a mouse, a keyboard, a touch panel, and/or the like.

The display 430 is connected to the processing circuitry 450 and is configured to display various types of information and various types of medical images output from the processing circuitry 450. For example, the display 430 is realized by using a liquid crystal monitor, a Cathode Ray Tube (CRT) monitor, a touch panel, or the like.

The storage 440 is connected to the processing circuitry 450 and is configured to store therein various types of data. For example, the storage 440 is realized by using a semiconductor memory element such as a Random Access Memory (RAM), a flash memory, or the like, or a hard disk, an optical disk, or the like. In the present embodiment, the storage 440 is configured to store therein the medical image data received from the medical image diagnosis apparatus 100 or the server apparatus 200, as well as the biopsy information received from the examination apparatus 300, processing results obtained by the processing circuitry 450, and the like.

In response to an input operation received from the operator via the input interface 420, the processing circuitry 450 is configured to control constituent elements of the medical information processing apparatus 400. For example, the processing circuitry 450 is realized by using a processor. In the present embodiment, the processing circuitry 450 is configured to store, into the storage 440, the medical image data, the biopsy information, the processing results, and the like output from the communication interface 410. Further, the processing circuitry 450 is configured to read any of the various types of information, the medical image data, and the like from the storage 440, to perform various types of processes thereon, and to cause the display 430 to display processing results.

A configuration of the medical information processing system including the medical information processing apparatus 400 has thus been explained. The medical information processing apparatus 400 according to the present embodiment configured as described above makes it possible to predict an examination result of a pathological examination based on a medical image with a high level of precision. More specifically, the medical information processing apparatus 400 is configured to generate and accumulate therein pieces of relevance information in each of which an image feature value of a tissue collected in a pathological examination is kept in correspondence with the examination result of the pathological examination performed on the tissue. As a result, by referring to the pieces of relevance information, it is possible to predict an examination result of pathological examination on the basis of an image feature value of a medical image, with a high level of precision.

As illustrated in FIG. 1, the storage 440 according to the present embodiment stores therein, for example, image information 441, biopsy information 442, and relevance information 443. Further, the processing circuitry 450 according to the present embodiment executes a controlling function 451, a first obtaining function 452, a second obtaining function 453, a calculating function 454, and a predicting function 455. In this situation, the processing circuitry 450 is an example of the processing circuitry.

Figure 3:
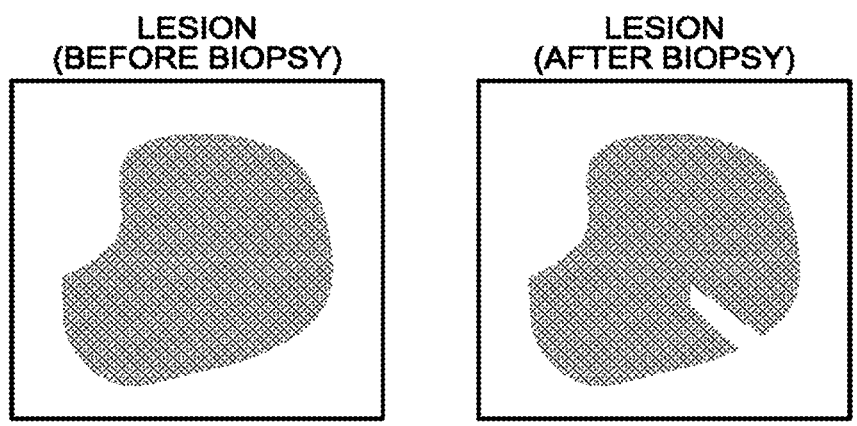
FIG. 3 is a drawing illustrating examples of image information according to the first embodiment.

The image information 441 is medical image data and/or medical images acquired in a medical examination. The image information 441 is obtained by the processing circuitry 450 either from the medical image diagnosis apparatus 100 or from the server apparatus 200. In this situation, the medical image data obtained by the processing circuitry 450 may be three-dimensional medical image data (volume data) acquired by the medical image diagnosis apparatus 100. In this situation, the image information 441 includes medical image data and medical images acquired before and after a biopsy. FIG. 3 is a drawing illustrating examples of the image information 441 according to the first embodiment. For example, as illustrated in FIG. 3, the image information 441 is represented by a medical image of a lesion before a biopsy and an image of the lesion after the biopsy. In this situation, the medical image of the lesion before the biopsy and the image of the lesion after the biopsy are kept in correspondence with identification information (e.g., the patient's ID, an examination ID of the pathological examination, etc.) used for uniquely identifying the correspondence with the biopsy information. In other words, the image information 441 is information in which the images are kept in correspondence with the identification information.

Further, the image information 441 includes medical image data and medical images of a plurality of image types related to mutually the same target site of mutually the same patient. For example, when the medical images before and after the biopsy illustrated in FIG. 3 are CT images, the image information 441 may include MR images, ultrasound images, PET images, and/or the like of the same lesion. In other words, from the patient, one or more CT images, MR images, ultrasound images, PET images and/or the like of the same lesion are acquired before the biopsy (before collecting the tissue) and one or more CT images, MR images, ultrasound images, PET images, and/or the like of the same lesion are acquired after the biopsy (after collecting the tissue). Further, when the medical images before and after the biopsy illustrated in FIG. 3 are CT images, the image information 441 may include CT images or the like acquired by using an X-ray energy level different from that for the CT images illustrated in FIG. 3.

As explained above, the storage 440 is configured to store therein the image information 441 represented by the medical image data and the medical images before and after a biopsy, for each of the target sites including a tissue on which a pathological examination is performed. Further, as the image information 441, the storage 440 is configured to store therein medical image data and medical images of a site on which no pathological examination is performed. For example, for the patient from whom the medical images illustrated in FIG. 3 were acquired, the storage 440 stores therein medical image data and medical images of a site different from the lesion illustrated in FIG. 3. In one example, the storage 440 stores therein a medical image including a site on which no pathological examination is performed but is suspected to be a tumor.

The biopsy information 442 is the examination information of the pathological examination obtained by the examination apparatus 300 and is obtained from the examination apparatus 300 by the processing circuitry 450. For example, the biopsy information 442 is information in which a morphological diagnosis result from a cytodiagnosis examination or a tissue examination is kept in correspondence with the identification information of the tissue on which the pathological examination was performed. In another example, the biopsy information 442 is information in which an examination result (e.g., the expression intensity score of a molecular marker) from a molecular pathological examination is kept in correspondence with identification information of the tissue on which the medical examination was performed.

In this situation, in the biopsy information 442, each of the pieces of identification information of the tissues is kept in correspondence with examination results of all the pathological examinations performed thereon. For example, a tissue collected from a target site is often sectioned into a plurality of tissue pieces, so that mutually-different pathological examinations are performed on the separate tissue pieces. In one example, a tissue collected from a target site is sectioned into a plurality of tissue pieces so as to calculate an expression score of a molecular marker by implementing each of the processes of immunostaining, in-situ hybridization, and a method based on an RT-PCR. Accordingly, in the biopsy information 442, each of the collected tissues is kept in correspondence with the examination results of the pathological examinations performed thereon.

The relevance information 443 is information in which image feature values of the tissue on which the pathological examination was performed are kept in correspondence with the biopsy information. The relevance information 443 is generated by a process performed by the processing circuitry 450 and is stored in the storage 440. FIG. 4 is a table illustrating an example of the relevance information 443 according to the first embodiment. For example, as illustrated in FIG. 4, the relevance information 443 is information in which "clinical cases", "scores (marker A)" and "feature values" are kept in correspondence with one another. In this situation, the "clinical cases" denote symptoms of diseases or diagnosis results. Further, the "scores (marker A)" denote the expression intensity scores of the molecular marker calculated by the examination apparatus 300. Further, the "feature values" denote the image feature values obtained from the image information by the processing circuitry 450. In this situation, "feature value A" to "feature value F" illustrated in FIG. 4 are image feature values each of which was obtained from an image of a different one of mutually-different image types.

For example, the storage 440 stores therein a piece of relevance information 443 indicating "clinical case: 1; score (marker A): 4; feature value A: 1; feature value B: 1; feature value C: 5; feature value D: 2; feature value E: 0; and feature value F: 1". In this situation, the numerical values of the feature values are predetermined index values. Similarly, the storage 440 stores therein the relevance information 443 in which, for each of the clinical cases, an expression intensity score of the molecular marker is kept in correspondence with an image feature value. The relevance information 443 illustrated in FIG. 4 is merely an example. Examples of the image feature values that can be kept in correspondence are not limited to those illustrated in FIG. 4. In other words, not y the predetermined index values, but also other various statistic values may be kept in correspondence. Further, although FIG. 4 illustrates the example in which a single "score" is kept in correspondence, a plurality of "scores" may be kept in correspondence.

Returning to the description of FIG. 1, the controlling function 451 included in the processing circuitry 450 is configured to exercise overall control of the medical information processing apparatus 400. For example, the controlling function 451 stores, into the storage 440, the medical image data, the medical images, the biopsy information, and the like output from the communication interface 410. Further, the controlling function 451 causes various types of processes to be performed in response to input operations received from the operator via the input interface 420. Further, the controlling function 451 causes the storage 440 to store the relevance information 443 therein and causes the display 430 to display various types of processing results obtained by the processing circuitry 450. Further, the controlling function 451 is also capable of causing an external apparatus such as the server apparatus 200 to store therein any of the processing results obtained by the processing circuitry 450. For example, the controlling function 451 is also capable of causing the server apparatus 200 to store therein the relevance information 443.

The first obtaining function 452 is configured to identify the position of a tissue from first medical image data represented by an image of a target site acquired before the tissue in the target to was collected and to obtain an image feature value of the tissue. More specifically, the first obtaining function 452 compares the first medical image data with second medical image data represented by an image of the target site acquired after the tissue was collected and further obtains the image feature value of the tissue based on a change between the first medical image data and the second medical image data. For example, the first obtaining function 452 obtains the image feature value of the tissue based on difference information between the first medical image data represented by the image of the target site acquired before the tissue in the target site was collected and the second medical image data represented by the image of the target site acquired after the tissue was collected. In other words, the first obtaining function 452 identifies, within the images, the pixels corresponding to the tissue in a pathological examination by calculating the difference between the first medical image data and the second medical image data and obtains the feature values of the identified pixels.

In this situation, when a tissue is collected in a pathological examination, distortion occurs in the target site. To cope with this situation, the first obtaining function 452 performs a position alignment for the purpose of correcting the distortion of the tissue occurring after the biopsy. More specifically, the first obtaining function 452 obtains the image feature value of the tissue by calculating the difference information between the first medical image data and the second medical image data, after performing a non-linear position alignment between the first medical image data and the second medical image data. The non-linear position alignment performed by the first obtaining function 452 may be performed by using any of publicly-known techniques.

After that, the first obtaining function 452 identifies the pixels corresponding to the tissue collected for the biopsy, by calculating the difference between the first medical image data and the second medical image data on which the position alignment has been performed. For example, the first obtaining function 452 performs the position alignment on a first medical image generated from the first medical image data and a second medical image generated from the second medical image data, and after the position alignment, identifies the pixels corresponding to the tissue collected for the biopsy, by calculating the differences in the pixel values between the pixels in the first medical image and the corresponding pixels in the second medical image.

In this situation, by comparing the difference value for each of the corresponding set of pixels between the first medical image and the second medical image, the first obtaining function 452 judges whether or not the pixel is a pixel corresponding to the tissue collected for the biopsy. In other words, the pixels corresponding to the tissue collected for the biopsy have a larger change in the pixel values thereof than other pixels do. For this reason, the first obtaining function 452 determines that such a position where the difference information exceeds a predetermined threshold value as the position of the tissue and further obtains the image feature value of the position of the tissue. In this situation, the threshold value may arbitrarily be set by the user or may automatically be set on the basis of information about changes in the pixel values between before and after the biopsy. Further, the threshold value may be set for each of various image types and for each of various target sites.

In this situation, the process of identifying the pixels corresponding to the tissue collected for the biopsy may be performed after the position alignment is performed on the entire image as described above. However, to improve the level of precision of the position alignment and to shorten the processing time period, it is also acceptable to perform the position alignment only on a predetermined region including the tissue. In that situation, the first obtaining function 452 performs a non-linear position alignment between a first region including the position of the tissue within the first medical image data and a second region including the position of the tissue within the second medical image data and further obtains the image feature value of the tissue by calculating the difference information between the first region and the second region.

Figure 5:
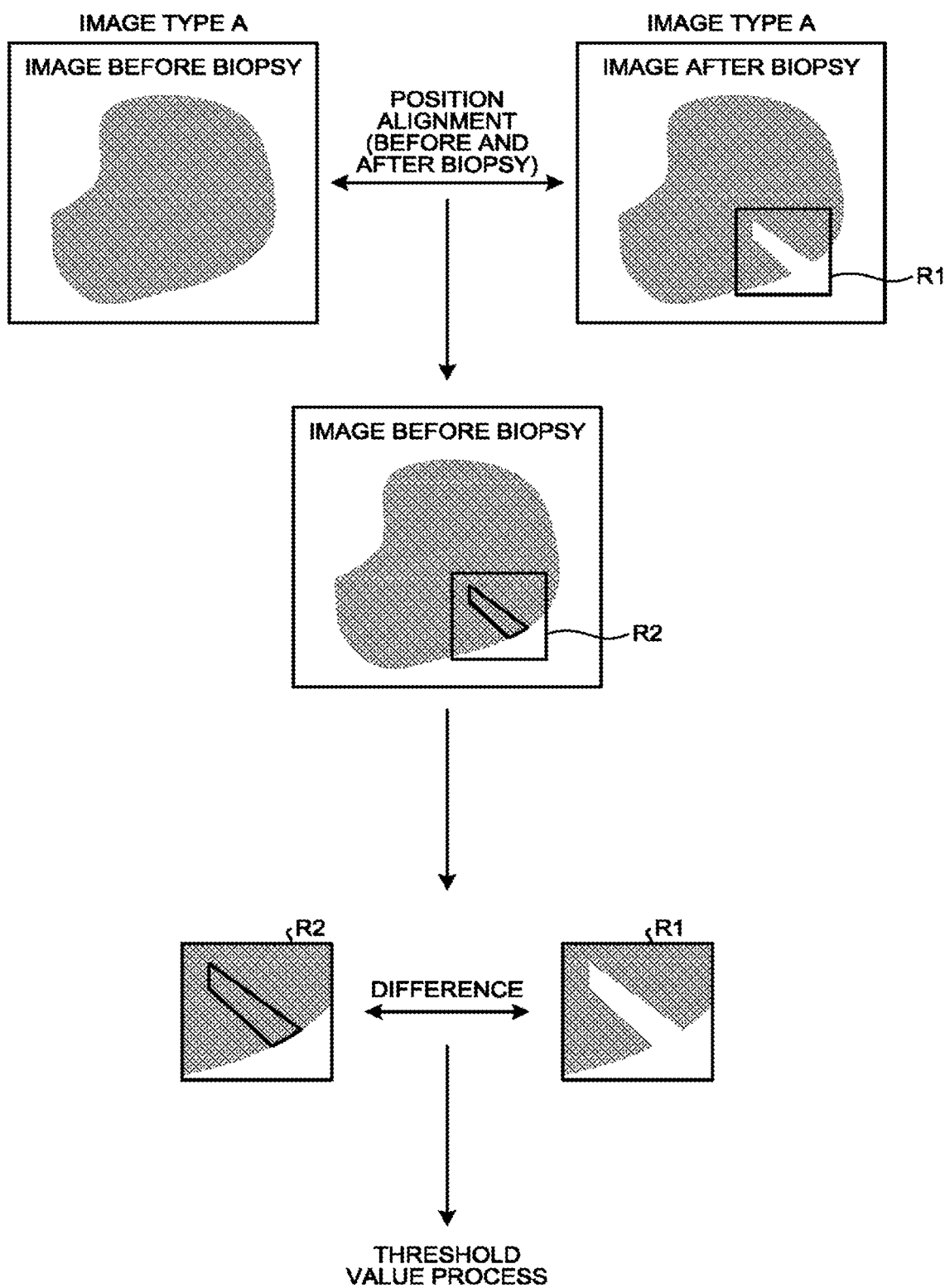
FIG. 5 is a drawing for explaining an example of a process of identifying pixels corresponding to a tissue performed by a first obtaining function according to the first embodiment.

FIG. 5 is a drawing for explaining an example of the process of identifying the pixels corresponding to the tissue performed by the first obtaining function 452 according to the first embodiment. For example, as illustrated in FIG. 5, when performing a position alignment on images before and after a biopsy that are of image type A, the controlling function 451 at first causes the display 430 to display the image after the biopsy acquired after the tissue was collected for the biopsy. The input interface 420 receives an operation to designate a region R1 including the tissue, from the user.

By performing a position alignment between the site included in the region R1 received by the input interface 420 with the image before the biopsy, the first obtaining function 452 extracts a region R2, which is a region within the image before the biopsy that corresponds to the region R1. After that, the first obtaining function 452 identifies a group of pixels corresponding to the tissue collected for the biopsy by calculating the differences between the pixel values of the pixels included in the region R1 and the pixel values of the corresponding pixels in the region R2 and further comparing the difference values with the threshold value.

As explained above, when having identified the group of pixels corresponding to the tissue collected for the biopsy, the first obtaining function 452 obtains a feature value (an image feature value) of the group of pixels corresponding to the tissue collected for the biopsy. In this situation, the first obtaining function 452 is able to obtain an arbitrary feature value, as the image feature value. For example, as the image feature value, the first obtaining function 452 may calculate any of various types of statistic values such as an average pixel value or a variance among the pixel values of the identified group of pixels, or an index value expressed as a sum of products of each pixel value and the frequency of appearance thereof. As other examples, the first obtaining function 452 is also able to calculate, as the image feature value, a feature value indicating a change in the contrast of the group of pixels. The first obtaining function 452 calculates the image feature value described above for each of the image types. Further, the first obtaining function 452 is also capable of calculating a plurality of feature values from one image type. Further, the number of feature values to be calculated may be different among various image types.

Figure 6:
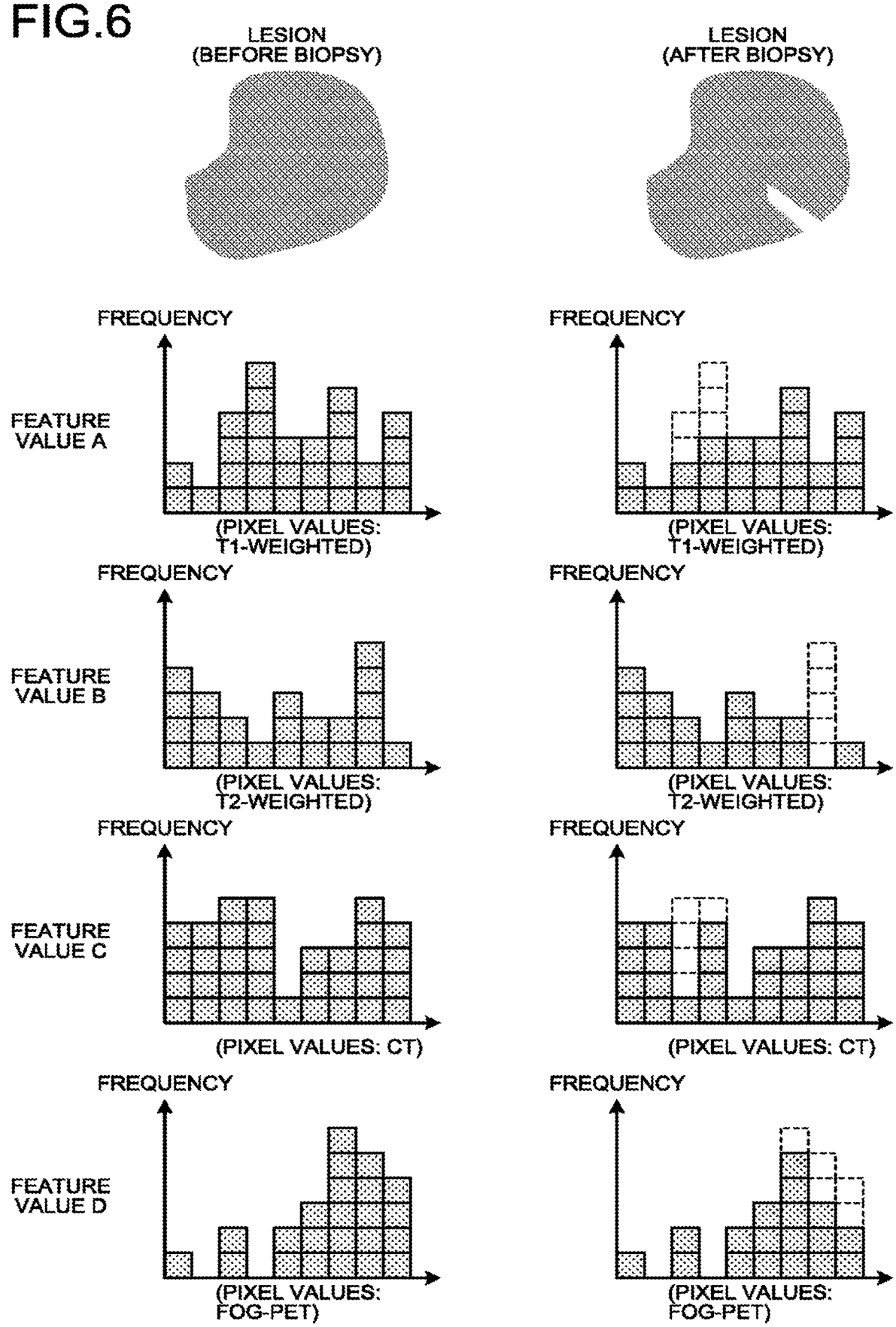
FIG. 6 is a drawing for explaining an example of a feature value calculating process performed by the first obtaining function according to the first embodiment.

FIG. 6, is a drawing for explaining an example of a feature value calculating process performed by the first obtaining function 452 according to the first embodiment. In this situation, FIG. 6 illustrates an example in which image feature values are calculated from differences in the histograms (pixel value profiles of the collected tissue) of the pixel values between before and after a biopsy, with respect to four image types (MR T1-weighted images, MR T2-weighted images, CT images, and FDG-PET images). Depicted in the top section of FIG. 6 is the target site before and after the biopsy from which the images of the four image types were acquired. Further, the histograms are arranged in the following order from top to bottom: histograms of the MR T1-weighted images, histograms of the MR T2-weighted images, histograms of the CT images, and histograms of the FDG-PET images. The histogram positioned on the left is a histogram before the biopsy, whereas the histogram positioned on the right is a histogram after the biopsy.

For example, for each of the image types, the first obtaining function 452 generates the histograms illustrated in FIG. 6 and calculates an image feature value by extracting pixel values of the pixels corresponding to the tissue collected for the biopsy, on the basis of the changes in the histograms between before and after the biopsy. In one example, the first obtaining function 452 generates a histogram of the pixel values of the lesion before the biopsy. Further, the first obtaining function 452 generates a histogram of the pixel values of the other pixels excluding the pixels corresponding to the tissue with respect to the lesion after the biopsy. After that, the first obtaining function 452 calculates an image feature value from the changes in the histogram between before and after the biopsy. For example, in the example of the T1-weighted images (the example of feature value A), the pixel values of the tissue exhibit relatively small values in the entire image, as illustrated in FIG. 6. For each of the image types, the first obtaining function 452 extracts such a pixel value profile of the tissue as the image feature value.

As explained above, the first obtaining function 452 is configured to calculate an image feature value for each of the image types. In this situation, the first obtaining function 452 is also capable of correcting differences in the image taking conditions among the various image types. For example, when calculating an image feature value from predetermined CT images (the CT images before and after the biopsy), the first obtaining function 452 calculates the image feature value from the predetermined CT images after performing a correcting process on the predetermined CT images so that various types of parameters included in the image taking condition become similar to those of a CT image obtained under a predetermined condition. In other words, when calculating the image feature value, the first obtaining function 452 is also capable of performing the correcting process to arrange the image taking conditions to be the same as each other, for each of the image types. As a result, in the relevance information 443 stored in the storage 440, it is possible to have image feature values stored in correspondence with each other from which differences that may be caused by the difference in the image taking conditions have been eliminated. In this situation, it is possible to arbitrarily set the predetermined condition for the various types of parameters.

Returning to the description of FIG. 1, the second obtaining function 453 is configured to obtain an examination result of the pathological examination performed on the tissue. More specifically, the second obtaining function 453 obtains the examination information (the biopsy information) of the pathological examination stored in the examination apparatus 300 and stores the obtained examination information into the storage 440. For example, the second obtaining function 453 obtains an examination result related to expression of a molecular marker at the tissue.

As explained above, when the first obtaining function 152 has obtained the image feature value and the second obtaining function 453 has obtained the biopsy information, the controlling function 451 is configured to generate the relevance information in which these pieces of information are kept in correspondence with one another and to store the generated relevance information into the storage 440. For example, the controlling function 451 generates the relevance information in which the image feature value and the biopsy information are kept in correspondence with each other on the basis of the identification information such as the patient's ID, the examination ID of the pathological examination, and the like and further stores the generated relevance information into the storage 440. In one example, the controlling function 451 generates the relevance information 443 illustrated in FIG. 4 and stores the generated relevance information 443 into the storage 440.

In this situation, the controlling function 451 sequentially generates/updates a piece of relevance information every time an image feature value and a piece of biopsy information are obtained so as to accumulate pieces of relevance information therein. The relevance information may be stored not only in the storage 440, but also in the server apparatus 200 or the like, as appropriate.

The calculating function 454 is configured to calculate an image feature value of medical image data on which a prediction for a pathological examination is to be made. For example, the calculating function 454 calculates an image feature value of a target site from medical image data of the patient acquired before a tissue is collected. In this situation, the calculating function 454 is able to calculate the image feature value similar to that calculated by the first obtaining function 452. In other words, the calculating function 454 is capable of calculating an image feature value for each of the image types. For example, similarly to the first obtaining function 452 described above, the calculating function 454 is capable of calculating the image feature value after performing a correcting process to arrange the image taking conditions to be the same as each other, with respect to the medical image data on which the prediction is to be made. When the correcting process to arrange the image taking conditions to be the same is performed, the correcting process is performed by making the same corrections as those that were made when the image feature value kept in correspondence within the relevance information 443 was calculated. Further, examples of the medical image data on which the prediction for the pathological examination is to be made include a medical image of the patient from which a suspicious lesion has newly been found while the medical image is being interpreted; and a medical image of a site (a metastatic lesion) different from the target site where the tissue was collected with respect to the patient on whom the pathological examination was performed.

Figure 7:
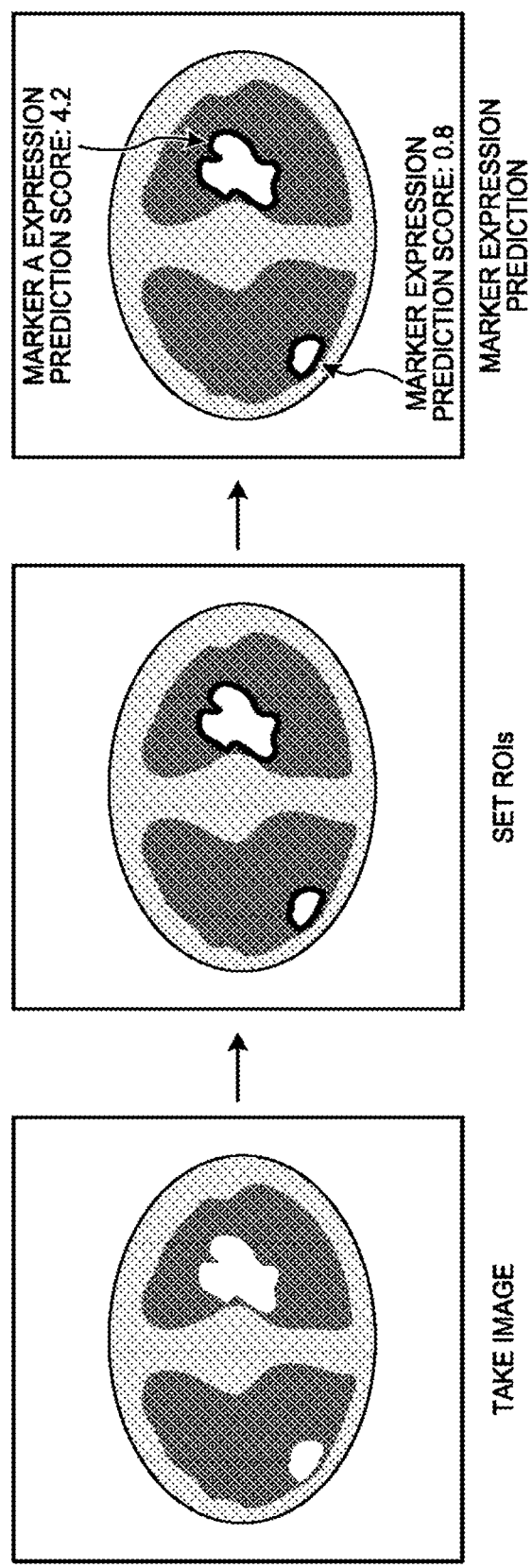
FIG. 7 is a drawing for explaining an example of a predicting process performed by a predicting function according to the first embodiment.

On the basis of the relevance information, the predicting function 455 is configured to predict an examination result of the pathological examination performed on the site different from the target site. More specifically, on the basis of the relevance information stored in the storage 440, the predicting function 455 predicts the result that would be obtained when a pathological examination is performed on the site of which the image feature value has been calculated by the calculating function 454. As for the prediction of the examination result made by the predicting function 455, the level of precision of the prediction is improved in the situation where the correcting process is performed to arrange the image taking conditions to be the same during the calculations of the image feature values at the time of generating the relevance information and at the time of predicting the examination result. FIG. 7 is a drawing for explaining an example of the predicting process performed by the predicting function 455 according to the first embodiment. FIG. 7 illustrates an example in which a prediction is made on expression of a molecular marker.

For example, as illustrated in FIG. 7, when the user has set two regions of interest (ROIs) in a taken image, the calculating function 454 calculates an image feature value of each of the ROIs. After that, on the basis of the image feature values of the ROIs calculated by the calculating function 454, the predicting function 455 predicts the expression of a molecular marker for each of the ROIs. For example, as illustrated in FIG. 7, the predicting function 455 calculates "marker expression prediction score: 4.2" for one of the ROIs. Further, the predicting function 455 calculates "marker expression prediction store: 0.8" for the other ROI.

In this situation, the predicting function 455 is able to make the prediction on the basis of any of various analyzing methods. In other words, the predicting function 455 is able to use, as appropriate, an analyzing method suitable for the volume and quality of the relevance information 443 accumulated in the storage 440. In other words, the calculating function 454 calculates one or more image feature values (e.g., a predetermined image feature value or a predetermined set of image feature values) corresponding to the accumulated relevance information 443, whereas the predicting function 455 predicts the result by using the calculated one or more image feature values.

In the explanation above, the example is explained in which the user sets the ROIs in the taken image; however, possible embodiments are not limited to this example. Another arrangement is also acceptable in which regions specified by a Computer-Aided Diagnosis (CAD) scheme are set as ROIs.

Processing functions of the processing circuitry 450 have thus been explained. In this situation, for example, the processing functions described above are stored in the storage 440 in the form of computer-executable programs. By reading each of the programs from the storage 445 and executing the read program, the processing circuitry 450 realizes the processing function corresponding to the program. In other words, the processing circuitry 450 that has read the programs has the processing functions illustrated in FIG. 1.

Further, with reference to FIG. 1, the example was explained in which the processing functions are realized by the single processing circuit (i.e., the processing circuitry 450); however, possible embodiments are not limited to this example. For instance, the processing circuitry 450 may be structured by combining together a plurality of independent processors, so that the processing functions are realized as a result of the processors executing the programs. Further, any of the processing functions of the processing circuitry 450 may be realized as being distributed to a plurality of processing circuits or being integrated into a single processing circuit, as appropriate.

Figure 8:
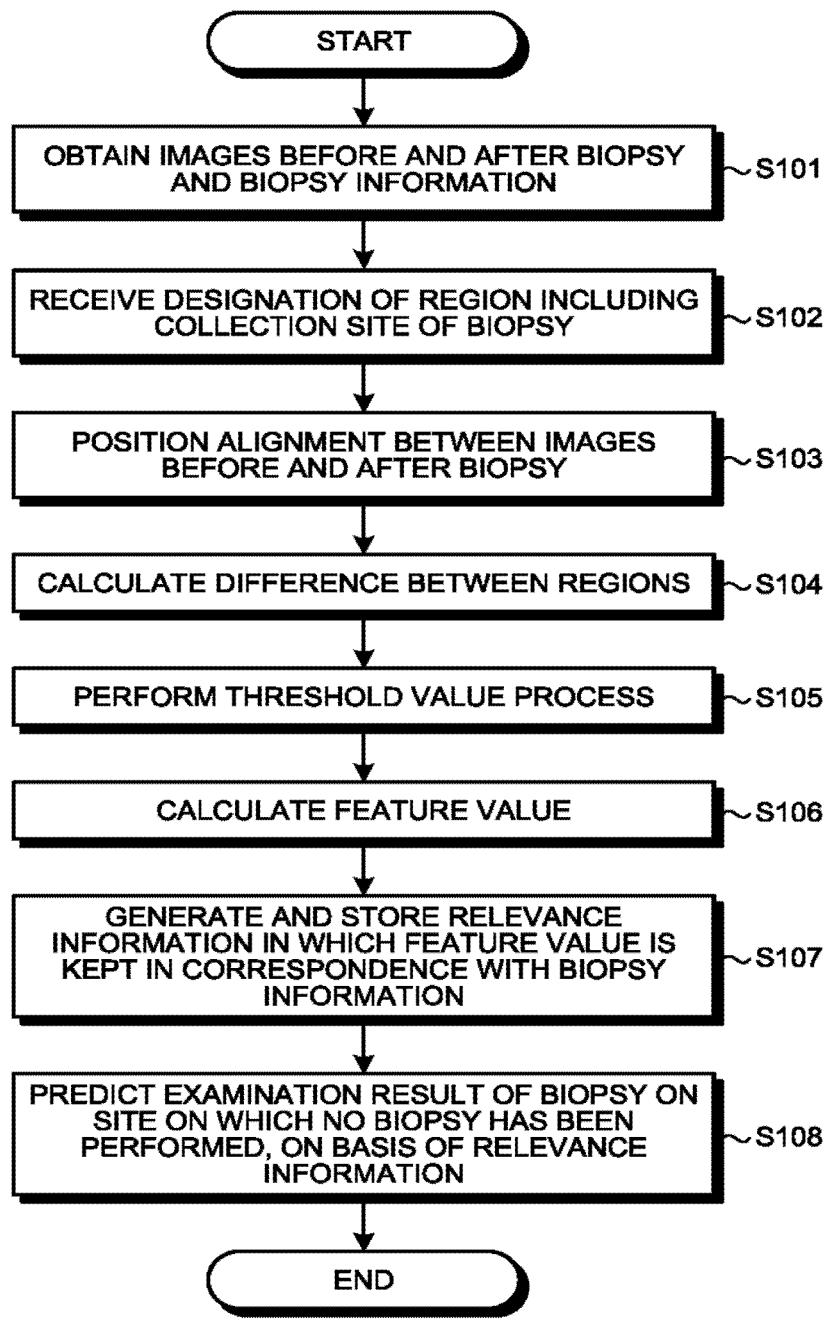
FIG. 8 is a flowchart illustrating a processing procedure performed by the medical information processing apparatus according to the first embodiment.
Figure 9:
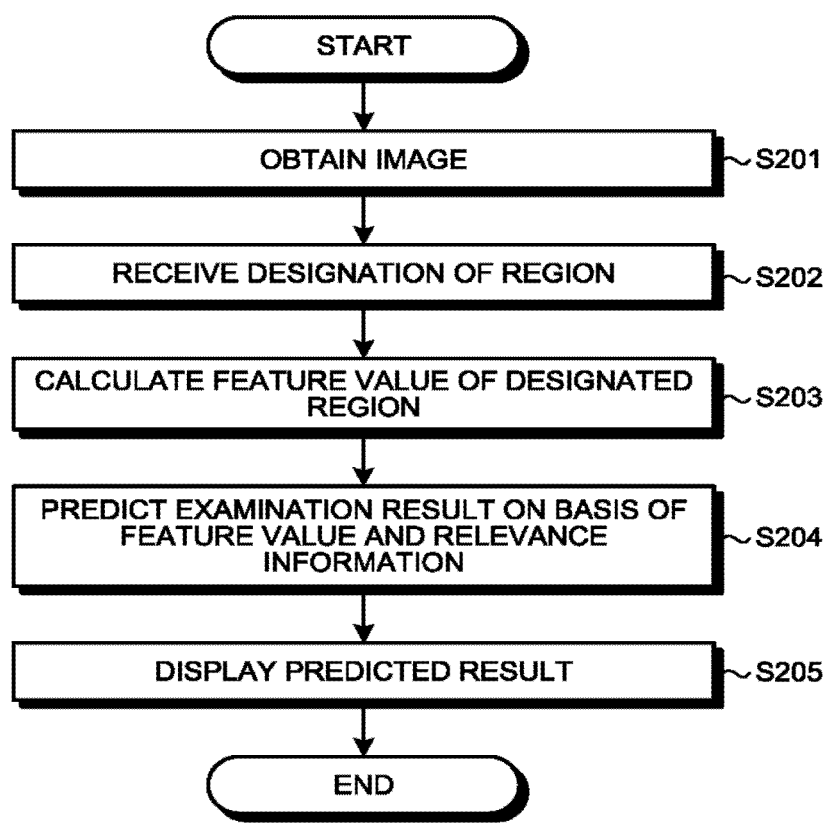
FIG. 9 is another flowchart illustrating the processing procedure performed by the medical information processing apparatus according to the first embodiment.

Next, a procedure in a process performed by the medical information processing apparatus 400 according to the first embodiment will be explained with reference to FIGS. 8 and 9. FIGS. 8 and 9 are flowcharts illustrating the processing procedure performed by the medical information processing apparatus 400 according to the first embodiment. FIG. 8 illustrates a process performed in a situation where regions are designated in an image, and pixels corresponding to a tissue are identified by calculating the difference between the designated regions. Further, FIG. 8 illustrates the process performed after the obtainment of medical image da a pathological examination, and a diagnosis by a medical doctor have been completed. FIG. 9 illustrates the process performed in a situation where an examination result is predicted with respect to an obtained image, by using the relevance information 443 accumulated in the storage 440. Also, FIG. 9 illustrates the situation where the region for which the examination result is to be predicted is designated by the user.

First, FIG. 8 will be explained. Steps S101, S102, and S107 in FIG. 8 are realized, for example, as a result of the processing circuitry 450 invoking and executing the programs corresponding to the controlling function 451 and the second obtaining function 453 from the storage 440. Further, steps S103 through S106 are realized, for example, as a result of the processing circuitry 450 invoking and executing the program corresponding to the first obtaining function 452 from the storage 440. Further, step S108 is realized, for example, as a result of the processing circuitry 450 invoking and executing the programs corresponding to the calculating function 454 and the predicting function 455 from the storage 440.

For example, as illustrated in FIG. 8, in the medical information processing apparatus 400 according to the present embodiment, the processing circuitry 450, at first, obtains images before and after a biopsy and biopsy information (step S101). Further, the processing circuitry 450 causes the display 430 to display the medical images and receives a designation of a region including the site from which a specimen was collected for the biopsy, via the input interface 420 (step S102).

After that, the processing circuitry 450 performs a position alignment on the images before and after the biopsy (step S103) and calculates the difference between the regions (step S104). Further, the processing circuitry 450 performs a threshold process (step S105) so as to identify a group of pixels corresponding to the tissue collected for the biopsy. Subsequently, the processing circuitry 450 calculates an image feature value (step S106).

After that, the processing circuitry 450 generates relevance information in which the image feature value and the biopsy information are kept in correspondence with each other and stores the generated relevance information into the storage 440 (step S107). After that, the processing circuitry 450 predicts an examination result of a biopsy of a site on which the biopsy has not been performed, on the basis of the relevance information (step S108).

Next, FIG. 9 will be explained. Steps S201, S202, and S205 in FIG. 9 are realized, for example, as a result of the processing circuitry 450 invoking and executing the program corresponding to the controlling function 451 from the storage 440. Further, step S203 is realized, for example, as a result of the processing circuitry 450 invoking and executing the program corresponding to the calculating function 454 from the storage 440. Step S204 is realized, for example, as a result of the processing circuitry 450 invoking and executing the program corresponding to the predicting function 455 from the storage 440.

For example, as illustrated in FIG. 9, in the medical information processing apparatus 400 according to the present embodiment, the processing circuitry 450, at first, obtains an image including a target site for which an examination result of a pathological examination is to be predicted (step S201). In this situation, the image including the target site which the examination result of the pathological examination is to be predicted may be the image used for generating the relevance information 443 or may be a new image that was not used for generating the relevance information 443. Further, the image including the targeting site used for which the examination result of the pathological examination is to be predicted may be an image acquired from an arbitrary examined subject.

After that, the processing circuitry 450 causes the display 430 to display the obtained image and receives a designation of a region via the input interface 420 (step S202). Further, the processing circuitry 450 calculates an image feature value of the designated region (step S203).

After that, the processing circuitry 450 predicts the examination result on the basis of the image feature value and the relevance information (step S204). Subsequently, the processing circuitry 450 causes the display 430 to display the predicted examination result (a predicted result) (Step S205).

With reference to FIG. 9, the example was explained in which the medical information processing apparatus 400 calculates the image feature value; however, possible embodiments are not limited to this example. For instance, another arrangement is also acceptable in which the medical information processing apparatus 400 obtains an image feature value calculated by another apparatus. In that situation, for example, the processing circuitry 450 obtains the image feature value calculated by the other apparatus and the image from which the image feature value was calculated. After that, the processing circuitry 450 predicts an examination result on the basis of the obtained image feature value and the relevance information and causes the predicted result to be displayed together with the obtained image.

As explained above, according to the first embodiment, the first obtaining function 452 is configured to obtain the image feature value of the tissue based on the difference information between the first medical image data represented by the image of the target site acquired before the tissue in the target site was collected and the second medical image data represented by the image of the target site acquired after the tissue was collected. The second obtaining function 453 is configured to obtain the examination result of the pathological examination performed on the tissue. The controlling function 451 is configured to store the relevance information in which the image feature value of the tissue and the examination result of the pathological examination are kept in correspondence with each other, into the storage 440. Consequently, the medical information processing apparatus 400 according to the first embodiment is able to have the pieces of relevance information accumulated in each of which an image feature value of a tissue on which a pathological examination was performed is kept in correspondence with the result of the pathological examination performed on the tissue. Accordingly, by using the pieces of relevance information, it is possible to make a prediction for the examination result of the pathological examination based on the medical image, with a high level of precision.

For example, in recent years, for treatments of cancer and the like, a molecular targeted therapy is performed by using therapeutic medication that acts while targeting a certain protein or gene (a molecular marker). It is expected that the effectiveness of the treatments is improved and that side effects are reduced. Such a molecular targeted therapy uses therapeutic medication that targets molecules (a protein or a gene) that are specifically expressed by cancer cells. In this situation, when a molecular targeted therapy is performed, it is checked, prior to the treatment, to see whether or not the molecular marker serving as the targeted molecules of the therapeutic medication is expressed by the cancer cells, for example, so that a treatment method (therapeutic medication) can be selected in accordance with the state of the expression. In this situation, when it is not possible to perform a biopsy due to a physical reason of the patient or due to a reason related to the site of the disease, is not possible to check to see whether or not the molecular marker serving as the targeted molecules of the therapeutic medication is expressed. It may therefore be impossible to perform an effective molecular targeted therapy in some situations. Even in those situations, the medical information processing apparatus 400 according to the present disclosure is able to predict an expression state of the molecular marker from the medical images of the patient, which as a result makes it possible to perform an effective molecular targeted therapy.

Further, according to the first embodiment, the first obtaining function 452 is configured to obtain the image feature value of the tissue, by calculating the difference information between the first medical image data and the second medical image data, after performing the non-linear position alignment between the first medical image data and the second medical image data. Consequently, the medical information processing apparatus 400 according to the first embodiment is able to identify the pixels corresponding to the tissue, after correcting the distortion of the site caused by the collection of the tissue, which therefore makes it possible to identify the position of the collected tissue more accurately.

Further, according to the first embodiment, the first obtaining function 452 is configured to obtain the image feature value of the tissue by performing the non-linear position alignment between the first region including the position of the tissue within the first medical image data and the second region including the position of the tissue in the second medical image data and further calculating the difference information between the first region and the second region. Consequently, the medical information processing apparatus 400 according to the first embodiment is able to perform the position alignment in a smaller area, which makes it possible to improve the level of precision of the position alignment and to shorten the processing time period.

Further, according to the first embodiment, the first obtaining function 452 is configured to determine such a position where the difference information exceeds the predetermined threshold value as the position of the tissue and to obtain the image feature value of the determined position of the tissue. Consequently, the medical information processing apparatus 400 according to the first embodiment makes it possible to identify the position of the collected tissue more accurately.

Further, according to the first embodiment, the first obtaining function 452 is configured to obtain the image feature value of the tissue based on the difference information with respect to each of the mutually-different image types. The controlling function 451 is configured to store, into the storage 440, the relevance information in which the image feature values of the tissue with respect to the various image types are further kept in correspondence with the examination result of the pathological examinations. Consequently, the medical information processing apparatus 400 according to the first embodiment is able to generate the relevance information containing the large number of pieces of information, which makes it possible to make the prediction with a high level of precision.

Further, according to the first embodiment, the second obtaining function 453 is configured to obtain the examination result related to the expression of the molecular marker at the tissue. The controlling function 451 is configured to store, into the storage 440, the relevance information in which the image feature values of the tissue are kept in correspondence with the examination result related to the expression of the molecular marker at the tissue. Consequently, the medical information processing apparatus 400 according to the first embodiment is able to accumulate the pieces of information related to the expression of the molecular marker, which makes it possible to predict the expression of the molecular marker.

Further, according to the first embodiment, the predicting function 455 is configured to predict the examination result of the pathological examination performed on the site different from the target site, on the basis of the relevance information stored in the storage 440. Consequently, the medical information processing apparatus 400 according to the first embodiment makes it possible to predict the result of the pathological examination by using the relevance information.

Second Embodiment

In the embodiment described above, the example is explained in which the images before and after the biopsy are acquired with respect to each of the various image types. In a second embodiment, an example will be explained in which images before and after a biopsy are acquired with respect to a single image type, and only images before the biopsy are acquired with respect to each of the other image types. The medical information processing apparatus 400 according to the second embodiment is different from the medical information processing apparatus 400 according to the first embodiment for the processes performed by the first obtaining function 452. In the following sections, the second embodiment will be explained while a focus is placed on the difference.

Figure 10:
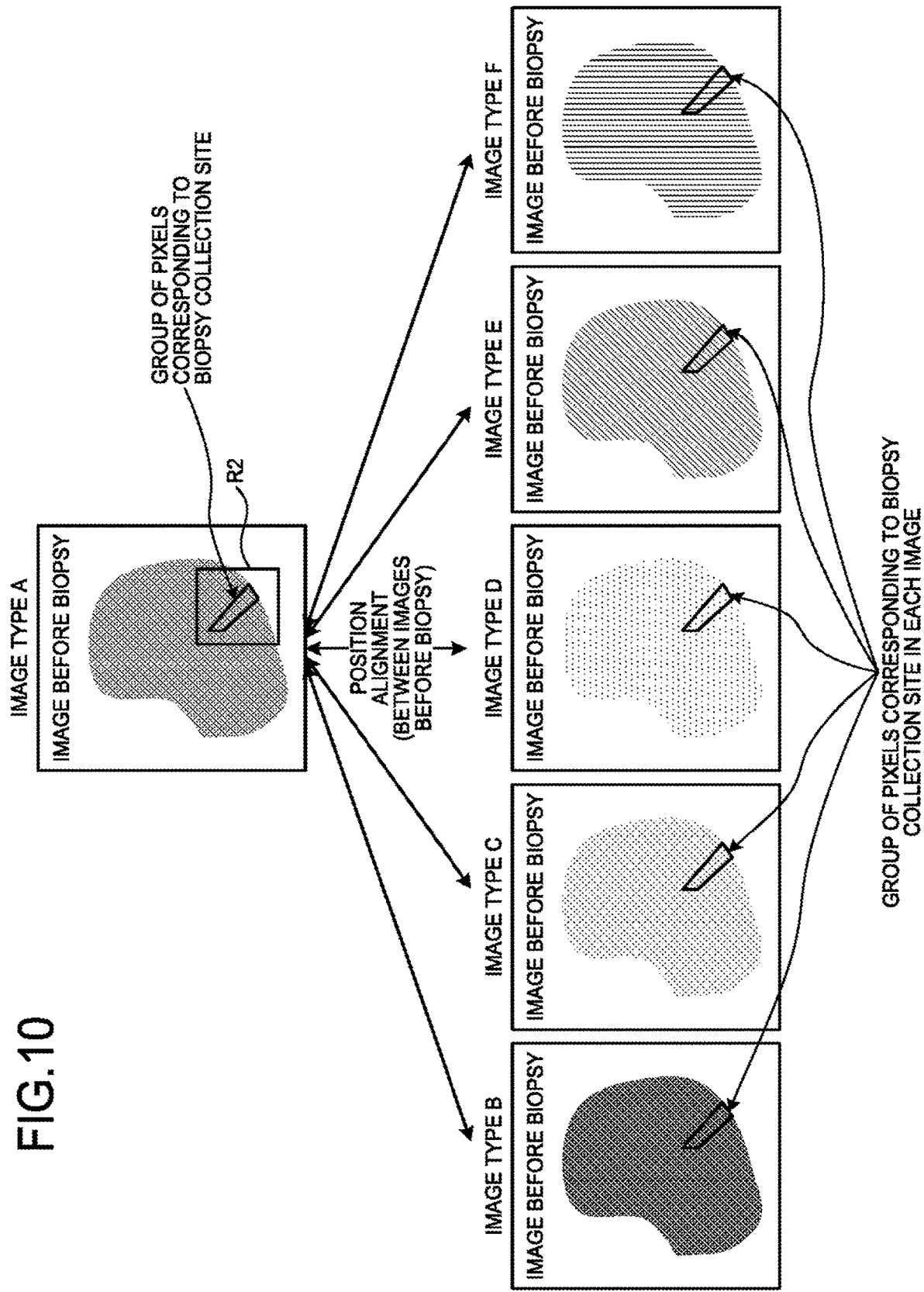
FIG. 10 is a drawing for explaining a process of identifying pixels corresponding to a tissue performed by a first obtaining function according to a second embodiment.

The first obtaining function 452 according to the second embodiment is configured to identify the position of a tissue in third medical image data by performing a position alignment between the first medical image data and the third medical image data that is of an image type different from that of the first medical image data and the second medical image data and is represented by an image of a target site acquired before the tissue was collected and to further obtain an image feature value of the position of the tissue in the third medical image data. FIG. 10 is a drawing for explaining an example of the process of identifying pixels corresponding to the tissue performed by the first obtaining function 452 according to the second embodiment. In this situation, FIG. 10 illustrates the process performed after pieces of medical image data of image type A before and after a biopsy have been acquired, and also, a group of pixels corresponding to the biopsy collection site has been identified by performing a position alignment between the regions.

For example, the first obtaining function 452 identifies the group of pixels corresponding to the biopsy collection site within each of the images, by performing a position alignment between the image of image type A before the biopsy and each of the images of image types B to F before the biopsy. In this situation, also in the position alignment performed among the images before the biopsy, the position alignment including distortion corrections is performed for the purpose of eliminating impacts of respiration and peristalses. For example, with respect to each of image types B to F, the first obtaining function 452 performs a position alignment with a region R2 of image type A by performing a non-linear position alignment process. As a result, the first obtaining function 452 is able to extract a group of pixels corresponding to the group of pixels in the biopsy collection site of image type A, from each of the images of image types B to F.

In this situation, because the position alignment is performed on the images of the mutually-different types, the significance of the pixel values varies. Accordingly, the first obtaining function 452 performs the position alignment process while taking into consideration relationships of pixel values among the mutually-different image types. For example, the first obtaining function 452 may perform the position alignment process by using a method for calculating an image mutual information amount or the like. Further, when the image types are different, the pixel sizes may vary in some situations. To cope with these situations, the first obtaining function 452 performs, for example, an interpolating process to match pixels having a larger pixel size with pixels having a smaller pixel size.

As explained above, according to the second embodiment, by performing the position alignment between the first medical image data and the third medical image data that is of the image type different from that of the first medical image data and the second medical image data and is represented by the image of the target site acquired before the tissue was collected, the first obtaining function 452 is configured to identify the position of the tissue in the third medical image data and to further obtain the image feature value of the position of the tissue in the third medical image data. The controlling function 451 is configured to store, into the storage 440, the relevance information in which the image feature value of the positions of the tissue in the third medical image data is further kept in correspondence with the examination result of the pathological examination. Consequently, the medical information processing apparatus 400 according to the second embodiment is able to reduce the number of images to be acquired after the biopsy, which makes it possible to reduce burdens on the patient.

Third Embodiment

The first and the second embodiments have thus been explained; however, it is possible to carry out the present disclosure in other various modes besides those in the first and the second embodiments described above.

In the embodiments described above, the example is explained in which the group of pixels corresponding to the tissue collected for the biopsy is identified by calculating the differences between the pixels in the medical images; however, possible embodiments are not limited to this example. For instance, when three-dimensional medical image data (volume data) has been acquired, it is also acceptable to identify a group of voxels corresponding to the tissue, by calculating the differences between the voxel values of the volume data. In that situation, it is possible to three-dimensionally identify the tissue collected for the biopsy.

Further, in the embodiments described above, the example is explained in which the expression of the molecular marker is predicted; however, possible embodiments are not limited to this example. For instance, it is also acceptable to obtain, as an image feature value, metabolic information of a polymer which can be obtained by using a PET apparatus and to further store the obtained image feature value so as to be kept in correspondence with a diagnosis result from a pathological examination. In that situation, the first medical image data and the second medical image data are represented by PET images. The first obtaining function 452 obtains the image feature value based on dynamics of a tracer at the tissue, on the basis of difference information between the first medical image data and the second medical image data.

For example, as the image feature value, the first obtaining function 452 obtains dynamics of the tracer with respect to a group of pixels corresponding to the tissue collection within a PET image acquired while using a protein that is specifically metabolized by predetermined type of cancer as the tracer. Further, the controlling function 451 stores, into the storage 440, relevance information in which a diagnosis on the collected tissue is kept in correspondence with the dynamics of the tracer obtained as the image feature value. The calculating function 454 obtains dynamics of the tracer in a site from which no tissue was collected. The predicting function 455 refers to the relevance information and judges whether or not the site from which no tissue was collected exhibits the predetermined type of cancer, on the basis of the dynamics of the tracer.

Further, in the embodiments above, the one example is explained in which the medical information processing apparatus 400 obtains the image feature values, has the relevance information stored, and performs the predicting process; however, possible embodiments are not limited to this example. For instance, the abovementioned processes may be performed while being distributed among a plurality of apparatuses included in the medical information processing system. For example, an image feature value may be calculated by each of the apparatuses included in the medical image diagnosis apparatus 100, so that the medical information processing apparatus 400 obtains the biopsy information from the examination apparatus, obtains the image feature values from the medical image diagnosis apparatus 100, and generates the relevance information.

The term "processor" used in the explanation of the above embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the storage, it is also acceptable to directly incorporate the programs in the circuits of the processors. In that situation, the processor realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof.

In this situation, the programs executed by the processors are provided as being incorporated, in advance, into a Read-Only Memory (ROM), a storage unit, or the like. Alternatively, the programs may be provided for those devices as being recorded on a computer-readable storage medium such as a Compact Disk Read-Only Memory (CD-ROM), a flexible disk (FD), a Compact Disk Recordable (CD-R), a Digital Versatile Disk (DVD), or the like, in a file that is in an installable format or in an executable format. Further, the programs may be stored in a computer connected to a network such as the Internet, so as to be provided or distributed as being downloaded via the network. For example, each of the programs is structured with a module including functional units. In actual hardware, as a result of a CPU reading and executing the programs from a storage medium such as a ROM, the modules are loaded into a main storage device so as to be generated in the main storage device.

According to at least one aspect of the embodiments described above, it is possible to predict the examination result of the pathological examination based on the medical images, with a high level of precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system comprising:
processing circuitry configured to
- identify a position of a tissue in first medical image data represented by an image of a target site acquired before the tissue in the target site was collected;
- calculate an image feature value of the tissue using pixel values of a plurality of pixels corresponding to the tissue in the first medical image data;
- obtain an examination result of a pathological examination performed on the tissue; and
- bring the image feature value of the tissue into association with the examination result of the pathological examination.

2. The medical information processing system according to claim 1, wherein the processing circuitry is configured to compare the first medical image data with second medical image data represented by an image of the target site acquired after the tissue was collected and identify the plurality of pixels corresponding to the tissue in the first medical image data based on a change between the first medical image data and the second medical image data.

3. The medical information processing system according to claim 2, wherein the processing circuitry is configured to identify the plurality of pixels corresponding to the tissue in the first medical image data by performing a subtraction between the first medical image data and the second medical image data.

4. The medical information processing system according to claim 3, wherein the processing circuitry is configured to perform the subtraction between the first medical image data and the second medical image data after performing a non-linear position alignment between the first medical image data and the second medical image data.

5. The medical information processing system according to claim 3, wherein the processing circuitry is configured to identify the plurality of pixels corresponding to the tissue in the first medical image data by performing a non-linear position alignment between a first region including the position of the tissue within the first medical image data and a second region including the position of the tissue within the second medical image data and further performing the subtraction between the first region and the second region.

6. The medical information processing system according to claim 3, wherein the processing circuitry is configured to determine such a position where a value after the subtraction exceeds a predetermined threshold value as the position of the tissue and calculate the image feature value of the tissue using pixel values of the plurality of pixels corresponding to the position of the tissue.

7. The medical information processing system according to claim 3, wherein
- the processing circuitry is configured to calculate the image feature value of the tissue on the basis of the subtraction between the first medical image data and the second medical image data with respect to each of mutually-different image types, and
- the processing circuitry is further configured to bring the image feature values of the tissue with respect to the various image types into association with the examination result of the pathological examination.

8. The medical information processing system according to claim 3, wherein
- by performing a position alignment between the first medical image data and third medical image data that is of an image type different from that of the first medical image data and the second medical image data and is represented by an image of the target site acquired before the tissue was collected, the processing circuitry is configured to identify the position of the tissue in the third medical image data and calculate an image feature value of the position of the tissue using pixel values of a plurality of pixels corresponding to the tissue in the third medical image data, and
- the processing circuitry is further configured to bring the image feature value of the position of the tissue in the third medical image data into association with the examination result of the pathological examination.

9. The medical information processing system according to claim 3, wherein
the processing circuitry is configured to
- obtain an examination result related to expression of a molecular marker at the tissue, and
- bring the image feature value of the tissue into association with the examination result related to the expression of the molecular marker at the tissue.

10. The medical information processing system according to claim 3, wherein
- the first medical image data and the second medical image data are represented by Positron Emission Tomography (PET) images, and
- the processing circuitry is configured to
  - obtain the image feature value based on dynamics of a tracer at the tissue, on a basis of the difference information between the first medical image data and the second medical image data, and
  - bring the image feature value based on the dynamics of the tracer at the tissue into association with the examination result of the pathological examination.

11. The medical information processing system according to claim 1, wherein the processing circuitry is further configured to predict an examination result of the pathological examination performed on a site different from the target site, on a basis of relevance information in which the image feature value of the tissue is kept in association with the examination result of the pathological examination.

12. A medical information processing apparatus comprising:
processing circuitry configured to
- identify a position of a tissue in first medical image data represented by an image of a target site acquired before the tissue in the target site was collected;
- calculate an image feature value of the tissue using pixel values of a plurality of pixels corresponding to the tissue in the first medical image data;
- obtain an examination result of a pathological examination performed on the tissue; and
- bring the image feature value of the tissue into association with the examination result of the pathological examination.

13. A medical information processing system comprising:
processing circuitry configured to
- calculate an image feature value of a target tissue using pixel values of a plurality of pixels corresponding to the target tissue included in medical image data;
- predict an examination result of a pathological examination performed on the target tissue from the image feature value of the target tissue, on a basis of relevance information in which image feature values of tissues are kept in association with examination results of pathological examinations performed on the tissues; and
- exercise control so as to output a result of the prediction made on the target tissue.

* * * * *